United States Patent
Kugler et al.

[11] Patent Number: 5,990,043
[45] Date of Patent: Nov. 23, 1999

[54] ANTI-FOULING COMPOSITIONS

[75] Inventors: Martin Kugler, Leichlingen; Michael Londershausen, Erkrath; Heinrich Schrage, Krefeld; Hermann Uhr, Leverkusen; Franz Kunisch, Odenthal, all of Germany

[73] Assignee: Bayer Aktiengesellschaft, Leverkusen, Germany

[21] Appl. No.: 08/652,571

[22] PCT Filed: Dec. 8, 1994

[86] PCT No.: PCT/EP94/04087

§ 371 Date: Jun. 17, 1996

§ 102(e) Date: Jun. 17, 1996

[87] PCT Pub. No.: WO95/17478

PCT Pub. Date: Jun. 29, 1995

[30] Foreign Application Priority Data

Dec. 21, 1993 [DE] Germany ............... 43 43 597
Mar. 17, 1994 [DE] Germany ............... 44 09 039

[51] Int. Cl.⁶ .......... A01N 43/40; A01N 43/50; A01N 47/34
[52] U.S. Cl. .......... 504/116; 504/150; 504/158; 504/159; 504/161; 424/405; 514/341; 514/351; 514/596; 514/597; 514/598
[58] Field of Search ............... 504/116, 150, 504/158, 159, 161; 424/405; 106/15.05, 18.32; 514/341, 351, 596, 597, 598

[56] References Cited

U.S. PATENT DOCUMENTS

| | | | |
|---|---|---|---|
| 3,679,466 | 7/1972 | Bowman, Jr. | 117/127 |
| 3,912,519 | 10/1975 | Takagi et al. | 424/277 |
| 4,468,405 | 8/1984 | Rigterink et al. | 424/322 |
| 4,818,534 | 4/1989 | Levy | 424/404 |
| 4,883,158 | 11/1989 | Twydell et al. | 514/616 |
| 4,923,894 | 5/1990 | Kanda et al. | 514/493 |
| 5,556,883 | 9/1996 | Thoms et al. | 514/594 |

FOREIGN PATENT DOCUMENTS

| | | |
|---|---|---|
| 111452 | 6/1984 | European Pat. Off. |
| 2402197 | 8/1974 | Germany. |
| 2614725 | 10/1976 | Germany. |
| 3024467 | 1/1982 | Germany. |
| 3414244 | 10/1985 | Germany. |
| WO 90 06975 | 6/1990 | WIPO. |
| WO 92 20747 | 11/1992 | WIPO. |

*Primary Examiner*—S. Mark Clardy
*Attorney, Agent, or Firm*—Sprung Kramer Schaefer & Briscoe

[57] ABSTRACT

An anti-fouling composition comprising a carrier, and a binder, the improvement which comprises an effective amount of at least one insecticide. The composition is applied to the surfaces of articles which come into contact with seawater or brackish water, especially wood. Other conventional anti-fouling agents may also be present.

7 Claims, No Drawings

ANTI-FOULING COMPOSITIONS

This application has been filed under 35 USC 371 as the national stage of international application PCT/EP94/04087 filed Dec. 8, 1994.

The invention relates to a process and compositions for protecting against infestation of articles, especially ships' hulls, screens, nets, constructions, quays and signalling equipment, which come into contact with seawater or brackish water.

Infestation by species of the group Lepadomorpha (goose barnacles), such as various Lepas and Scalpellum species, or by species of the group Balanomorpha (acom bamacles), such as Balanus or Pollicipes species, increases the frictional resistance of ships and leads as a result, through increased energy consumption and fent spells in dry dock, to a marked increase in the operating costs.

In addition to infestation by algae, for example Ectocarpus species and Cerarium species, particular importance attaches to infestation by sessile Entomostraca groups, which are comprised under the name Cirripedia (curiped crustacens).

It is known, in addition, that insects can be controlled by means of active substances which act on the metamorphosis from the larval stage to the adult insect (K. H. Büichel, Pflanzenschutz und Schädlingsbekämpftng [Plant protection and pest control], Georg Thieme Verlag, Stuttgart 1977 Farm Chemicals Handbook, Meister Publ. Comp. 1993; The Agrochemical Handbook, Third Edition, Royal Society of Chemistry, Cambridge 1991).

It has now been found that the insecticides, alone or in combination with other active substances, have an outstanding anti-fouling (anti-infestation) effect.

Since conventional anti-infestation compositions have a high content of heavy metals, for example tin or copper, it is of advantage here that by using the insecticides according to the invention it is now possible to dispense with the use of heavy metal compounds such as, for example, bis (trialkyltin) sulfides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulfide, antimony oxide, polymeric butyl titanate, phenyl-(bis-pyridine)-bismuth chloride, tri-n-butyltin fluoride, manganese ethylenebisdithiocarbamate, zinc dimethyldithiocarbamate, zinc ethylenebisdithiocarbamate, the zinc salt of 2-pyridinethiol 1-oxide, bisdimethyldithiocaibamoylzinc ethylenebisdithiocarbamate, zinc oxide, copper(I) ethylene-bis-dithiocarbanate, copper thiocyanate, copper naphthenate and tributyltin halides, or substantially to reduce the concentration of these compounds.

The application therefore relates to antifouling compositions comprising at least one insecticide.

Preference is given to insecticides having a development-inhibiting action which are capable of inhibiting the metamorphosis from crustacean larvae to the adult stage.

The insecticides which can be employed in accordance with the invention are generally known and can come from different structural classes.

Particularly preferred compounds in the context of the invention are benzoyl ureas such as triflumuron, chlorfluazuron, diflubermiron, flufenoxuron, flucycloxuron, hexaflumuron, penfluron, teflubenzron, nitroimines and nitromethylenes such as 1-[(6-chloro-3-pyridinyl)methyl]4,5-dihydro-N-nitro-1H-imidazol-2-amine (imidacloprid), N-[(6-chloro-3-pyriyl)methyl-]$N^2$-cyano-$N^1$-methylaceamides (NI-25); 1-[4-(4chlorophenoxy)-3,5-dichlorophenyl]-3-(2,6-difluoro-benzoyl)-urea and N-[[2,5-dichloro4-(1,1,2,3,3,3-hexafluoropropoxy)phenyl]-amino]-carbonyl]-2,6-difluorobenzamide.

Preference is likewise given to development inhibitors from other structrral classes, for example benzoic acid [2-benzoyl-1(1,1-dimethylethyl)]-hydrazide, 2,6-dimethoxy-N-[5-]4-(pentafluoroethoxy)phenyl[-1,3,4thiadiazol-2-yl]-bezamnide, N-cyclopropyl-1,3,5-triazine-2,4-triamine, 2-(4-phenoxyphenoxy)ethyl ethylcarbamate, 1-(decycloxy)-4[(6-methoxy4-hexinyl)-oxy]benzenes, (2-propinyl)4-methoxybenzoate, fenoxycarb, pyriproxyfen, triamathene, thiapronil, hexythiazox, clofentezine, 4-chloro-5-(6-chloro-3-pyridyhnethoxy)2-3,4dichlorophenyl) pyridazin-3(2H)ones, buprofezin, hydroprene, kinoprene, methoprene, cycloprate, gush padan, paraxon, tribunil, isomers and triprene.

The active compounds mentioned here are given only by way of example; structurally related active substances having an insecticidal or development-inhibiting action are likewise suitable in principle for anti-fouling use. The following insecticides may be given as preferred examples:

Phosphoric esters, such as azinphostyl, azinphos-methyl, -1(4-chlorophenyl)4-O-ethyl, S-propyl)phosphoryloxy-pymrl, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulprofos, triazophos and trichlorphon;

Carbamates, such as aldicarb, bendiocarb, -2-1-methylpropyl)phenyl methylcamate, butocarboxim, butoxycarboxim, carbaryl, carbofuran, carbosulfan, cloethocarb, isoprocarb, methomyl, oxamyl, pirimicarb, promecarb, propoxur and thiodicarb;

Organosilicon compounds, preferablydimethyl(phenyl) silyl-methyl 3-phenoxybenzyl ethers, such as dimethyl-(4-ethoxyphenyl)-silylmethyl 3-phenoxybenzyl ether, or [(dimethyl)phenyl)silyl-methyl 2-phenoxy-6-pyridylmethyl etherssuchasfor exampledimethyl(9-ethoxy-phenyl)-silylnethyl 2-phenoxy-pyridylmethyl ether, or [(phenyl)-3-(3-phenoxyphenyl)-propyl](dimethyl)-silanes, such as, for example, (4-ethoxyphenyl) [3-(4fluoro-3-phenoxyphenyl-propyl]dimethyl-silane, sulafluofen;

Pyrethroids such as allethrin, alphamcthrin, bioresmetrin, byfenthrin, cycloprothrin, cyfluthtin, decanethrin, cyhalothrin, cypermerin, deltaamethrin, alpha-cyano-3-phenyl-2-methylbenzyl-2,2-dimethyl-3-(2-chloro-2-trifluoromethylvinyl)cyclopropanecarboxylate, fenpropathrin, fenfluthrin, fenvalerate, flucythrinate, flumethrin, fluvalinate, permetlrin, resmethrin and tralomethrin;

abamectin, AC 303, 630, acephate, acrinathrin, alanycarb, aldeoxycarb, aldrin, amitraz, azamethiphos, bacillus thuringiensis, phosmet, phosphamidon, phosphine, prallethrin, propaphos, propetamphos, prothoate, pyraclofos, pyrethims, pyridaben, pyridafenthion, quinalphos, RH-7988, rotenone, sodium fluoride, sodium hexafluorosilicate, sulfotep, sulfuryl fluoride, tar oils, tefluthrin, temephos, terbufos, tetrachlorovinphos, tetrametrin, O-2-tert.-butyl-pyrimidin-5-yl-o-isopropyl-phosphorothiate, thiocyclam, thiofanox, thiometon, tralomethrin, triflumuron, trimethacarb, vamidothion, Verticillium, Lacanii, XMC, xylylcarb, benfiracarb, bensultap, bifenthrin, bioallethrin, MERbioallethrin, (S)-cyclopentenyl isomer, bromophos, bromophosethyl, cadusafos, calcium polysulphide, carbophenothion, cartap, chinomethionate, chlordane, chlorfenvinphos, chlormephos, chloropicrin, chlorpyrifos, cyanophos, beta-cyfluthrin, alphacypermethrin, cyophenothrin, cyromazine, dazomet, DDT, demeton-S-methylsulphon, diafenthiuron, dialifos, DEicrotophos, dinoseb, deoxabenzofos, diaxacarb, disulfoton, DNOC, empenthrin, endosulfan, EPN, esfenvalelrate, ethiofencarb, ethion, etofenprox, fenobucarb, fensulfothion, fipronil, flufenprox, fonofos, formetanate, formoothion, fosmethilan, furathocarb, heptachlor, IPSP, isazofos, isofenphos, isoprothiolane, isoxathion, iodifenphos, Kadethrin, lindane, malthion, mecarbam, mephosfolan, mercurous chloride, metam, Metarthizum anisopliae, methacrifos, methamidophos, methidathion, methiocarb, methoxychlor, methyl isothiocyanate, metholcarb, mevinphos, monocrotophos, naled, Neodidprion sertifer NPV, nicotine, omethoate, oxydemeton-methyl, pentachlorophenol, petroleum oils, phenothrin, phenthoate, phorate.

Furthermore, synergistic effects are observed in the case of combinations of two or more of the insecticides mentioned. The development inhibitors according to the invention are preferably also employed in combination with algicides, herbicides, fungicides, molluscicides and/or other anti-fouling active substances, in which case synergistic effects are likewise observed.

Co-cmponents which are employed with preference for the anti-fouling compositions according to the invention are algicides such as diuron, dichlorophen, endothal, fentin acetate, quinoclamine, molluscicides such as fentin acetate, metaldehyde, methiocarb, niclosamide, thiodicarb and trimethacarb, fungicides such as dichlofluanid, tolylfluanid, fluorfolpet, and azoles such as tebuconazole or customary anti-fouling active substances such as 2-(N,N-dimethylthiocarbamoylthio)-5-nitrothiazyl, tetrabutyldistannoxane, 2-tert-butylamino-4-cyclopropylamino-6-methylthio-1,3,5-triazine,4,5-dichloro-2-noctyl4-isothiazolin-3-one, 2,4,5,6tetrachloroisophthalonitrile, tetramethylthiuram disulfide, 2,4,6-trichlorophenylmaleimide,2,3,5,6-tetrachloro-4-(methylsulfonyl)-pyridine, diodrnethylparatrylsulfone, thiabendazol, tetrrphenylboron pyridine salt, potassium salt, sodium salt and zinc salt of 2-pyridinethiol 1-oxide.

The anti-fouling compositions according to the invention additionally contain the customary constituents as described, for examnple, in Ungerer, Chem. Ind. 37 (1985), 730–732 and Williams, Antifouling Marin Coatings 1973, Park Ridge: Noyes 1973.

Customary constituents in anti-fouling coating compositions are, in particular, binders.

Examples of binders are polyvinyl chloride in a solvent system, chlorinated rubber in a solvent system, acrylic resins in a solvent systenm, in particular in an aqueous system, vinyl chloride/vinyl acetate copolymer systems in the form of aqueous dispersions or in the form of organic solvent systems, butadiene/styrene rubbers, butadienejacrylonitrile rubbers, butadiene/styen/acrylonitrile rubbers, drying oils, such as linseed oil, asphalt and epoxy comnpounds, resin esters or modified hard resins in combination with tar or bitumen, chlorinated rubber, chlorinated polypropylene and vinyl resins.

The coating compositions may also contain inorganic pigments, organic pigments or dyes, which are preferably insoluble in seawater. The coating compositions may additionally contain materials such as rosin and/or rosin derivatives, in order to enable controlled release of the development inhibitors according to the invention. The coatings can additionally contain plasticizers, modifying agents which influence the rheological properties, and also other customary constituents. The compounds according to the invention or initially mentioned combinations can also be incorporated in self-polishing anti-fouling systems.

Formulation examples, in which the active substances and/or active-substance combinations described are preferably employed, are described in DE 27 32 145 and EP 05 26 441.

Moreover, it has been found surprisingly that the mixtures of the development inhibitors according to the invention with algicides, herbicides and fungicides can also be used as wood preservatives. These mixtures are in this case effective in particular against insects, moulds, woodiscolouring fumgi and wood-destroying fimgi.

The following groups of microorganisms may be mentioned by way of example, but without representing any limitation:

A: Wood-discolouring fungi:
A1: Ascomycetes Ceratocystis such as Ceratocystis minor
A2: Deuteromycetes:
  Aspergillus such as Aspergillus niger
  Aureobasidium such as Aureobasidium pullulans
  Dactylium such as Datylium fusarioides
  Penicillium such as Penicillium brevicaule or Penicillium variabile
  Scierophorna such as Sclerophoma pithyophila
  Scopularia such as Scopularia phycomyces
  Trichoderma such as Trichoderma viride or Trichoderma lignorum
A3: Zygomycetes Mucor such as Mucor spinorus
B: Wood-destroying fungi:
B1: Ascomycetes
  Chaetomium such as Chaetomium globosum or Chaetomium alba-arenulum
  Humicola such as Humicola grisea
  Petrella such as Petriella setifera
  Trichurus such as Trichurus spiralis
B2: Basidiomycetes:
  Coniophora such as Coniophora puteana
  Coriolus such as Coriolus versicolor
  Donkioporia such as Donkioporia expansa
  Glenospora such as glenospora gaphii
  Gloeophyllum such as Gloeophyllum abietinum or Gloeophyllum adoratum or Gl. Protactum or Gloeophyllum sepiarium or Gl. tabeum
  Lentinus such as Lentinus cyathifonmes or Lentinus edodes such as Lentinus lepideus or Lentinus grinus or L. squarlosus
  Paxillus such as Paxillus panuoides
  Pleurotus such as Pleurotus ostr
  Poria such as Poria monticola or Poria placenta or Poria vaillantii or Poria vaporaria
  Serpula such as Serpula hirantoides or Serpula lacrylans
  Stereum such as Stereum hirsutum
  Tyromyces such as Tyromyces palustris
B3: Deuteromycetes:
  Alternaria such as Alternaria tenius
  Cladosporium such as Cladosporium herbarumrn
C. Wood-destroying insects such as
C1: Beetles
  Hylotupes bajulus, Chlorophorus pilosis, Anobium puncttm, Xestobium rufovillosum, Ptilinus pecticomis, Dendrobium pertinex, Ernobius mollis, Priobium carpini, Lyctus brunneus, Lyctus aficanus, Lyctus planicollis, Lyctus linearis, Lyctus pubescens, Trogoxylon aequale, Minthes rugicollis, Xyleborus spec. Tryptodendron spec. Apate monachus, Bostrychus capucins, Heterobostrychus brunneus, Sinoxylon spec. Dinoderus minutus C2: Hymenoptera
Sirex juvencus, Urocerus gigas, Urocerus gigas taignus, Urocerus augur C3: Termites
Kalotermes flavicollis, Cryptotermers brevis, Heterotermes indicola, Reticulitermes flavipes, Reticulitermes santonensis, Reticulitermes lucilugus, Mastotermes darwiniensis, Zootermopsis nevadensis, Coptotermes fonnosanus.

These wood preservatives generally contain from 0.01 to 50% by weight of algicides, herbicides and/or fingicides and from 0.00001 to 10% by weight of insecticides. Furthermore, the wood preservatives generally contain more than 40% of a mixture of solvent and/or diluent and/or organic-chemical binders or fixative, processing agent, dye, pigment, dye mixture or pigment mixture.

The mixtures contain as algicides for example:
copper sulphate, dichlororphen, endothal, fentin acetate, quinoclamine;

as herbicides for example:
acetochlor, acifluorfen, aclonifen, acrolein, alachlor, alloxydim, ametryn, amidosulfiron, amitrole, ammonium sulfamate, anilofos, asulam atraine, aziptrotryne, benazlin, benfluralin, benfiresate, bensulfuron, bensulfide, bentazone, benzofencap, benzthiazuron, bifenox, bilanafos, borax, dichlorprop, dichlorprop-P, diclofop, diethatyl, difenoxuron, difenzoquat, diflufenican, dimefuron, dimepiperate, dimethachlor, dimethametryn, dimethipin, dimethylarsinic acid, dinitramine, dinoseb, dinoseb, dinoseb acetate, dinoseb, bromnacil, bromobutide, bromofenoxim, bromoxynil, butachlor, butamifos, fuenachlor, butralin, butylate, carbetamide, CGA 184927, chlorrethoxyfen, chloramben, chlorbromuron, chlorbutam, chlorfurenol, chloridazon, chlorimuron, chlornitrofen, chloroacetic acid, achloropicrin, chlorotoluron, chloroxuron, chlorprepham, chlorsulfuron, chlorial, chlorthiarnid, cinmethylin, cinofulsuron, clethodini, clomazone, clomeprop, clopyralid, cyanamide, cyanazine, dinoseb acetate, dinoterb, diphenamid, dipropetiyn, diquat, dithiopyr, diduron, DNOC, PPX-A 788, DPX-E96361, DSMA, eglinazine, endothal, EPTC, esprocarb, ethalfluralin, ethidimuron, ethofumesate, fenoxaprop, fenoxaprop-P, fenuron, flamprop, flamprop-M flazasulfuron, fluazifop, fluazifop-P, fluchloralin, flumeturon, fluorocgycofen, fluoronitrofen, flupropanate, flurenol, fluridone, flurochloridone, fluoroxypyr, cycloate, cycloxydim, 2,4-D, daimuron, dalapon, dazonet, 2,4-DB, desmedipharm, desmetryn, dicamba, dichlorbenil, isoproturon, isouron, isoxabe, isoxapyrifop, lactofen, lenacil, linuron, LS830556, MCPA, MCPA-thioethyl, MCPB, mecoprop, mecoprop-P, mefence, mefluidide, metam, metamiton, me or, me abiazuron, methazole, methoproptryne, methyldynron, methylisothiocyanate, metobromuron, fomosafen, fosamine, furyloxyfen, glufosinate, glyphosate, haloxyfop, hexazinone, imazamethabenz, imazapyr, imazaquin, imzethapyr, ioxynil, isopropalin, propyzamide, prosulfocab, pyrazolynate, pyrazolsulfuron, pyzazoxyfen, pyributicarb, pyridate, quinclorac, quinmerac, quinocloamine, quizalofop, quzizalofop-P, S-23121, sethoxydim, sifuron, simaine, simetryn, SMY 1500, sodium chlorate, sulfometuron, tar oils, TCA, metolachlor, metoxuron, metribzin, metsulfuron, molinate, monalide, monolinuron, MSMA, naproanilide, napropamide, naptalam, neburon, nicosulfuron, nipyraclofen, norflurazon, orbencarb, oaryzalin, oxadiazon, oxyfluorfen, paraquat, pebulate, pendimethalin, pentachlorophenol, pentaochlor, petroleum oils, phenmedipham, pichloram, piperophos, pretilachlor, primisulfuron, prodiamine, proglinazine, propmeton, prometryn, propachlor, tebutam, tebuthiuron, terbacil, terbumeton, terbuthylazine, terbutryn, thiazafluoron, thifensulfliron, thiobencarb, thiocarbazil, tioclorim, tralkoxydim, triallate, triasulfuron, tribenzuron, triclopyr, tridiphane, trietazine, trifluralin, IBI-C4874 vemolate, propanil, propaquizafop, propazine, propham.

Preferred mixtures contain fungicides such as hexaconazole, tebuconazole, propiconazole, cycproconazoleand/or 2-(1-chloro-cyclopropyl)1-2-chlorophenyl)3-1H-(1,2,4-triazol-1-yl)-propan-2-ol, preferably in a weight ratio with respect to the insecticide of from 1:9 to 9:1.

Preferred additional fungicidal co-components are also:
bromuconazole, dichlobutazol, diniconazole, penconazole, methyl (E)methoximino-[a-(o-tolyloxy) o-tolyl)]acetate, methyl [E]-2-{2-[6-(2-cyanophenoxy) pyrimidin4yl-oxy]phenyl}-3-methoxyacrylate, meroxamn, carboxin, fenpiclonil, 4(2,2-difluoro-1,3-benzodioxol-4-yl)-1H-pynrole-3-carbonitrile, butenafme and/or 3-iodo-2-propinyl n-butylcarbamate.

In addition it is possible to employ synergistically insecticidal co-components, such as the following insecticides:

phosphoric esters such as azinphos-ethyl, azinphos-methyl, α-1(4chlorophenyl)4(O-ethyl, S-propyl) phosphoryloxy-pyrazol, chlorpyrifos, coumaphos, demeton, demeton-S-methyl, diazinon, dichlorvos, dimethoate, ethoate. ethoprophos, etrimfos, fenitrothion, fenthion, heptenophos, parathion, parthion-methl, phosalone, phoxim, pmphosethyl, pirimiphos-methyl, profenofosm prothiofos, sulfprofos, triazophos and trichlorphon;

Carbamates such as aldicarb, bendiocarb, a-2-(1-methylpropyl)-phenyl methylcarbamate, butocarboxim, butoxycarboxim, carbaryl, carbofirn, carbosulfan, cloethocarb, isoprocarb, methomyl, oxamyl, pirimicarb, promecarb, propoxur and thiodicarb;

organosilicon compounds, preferably dimethyl(phenyl) silyl-methyl-3-phenoxybenzyl ethers, such as dimethyl-(4-ethoxyphenyl)silylmethyl 3-phenoxybenzyl ether, or (dimethylphenyl)silyl-methyl 2-phenoxy-6-pyridylmethyl ethers such as for example dimethyl(9-ethoxy-phenyl)-silylmethyl 2-phenoxy-6-pyridylmethyl ether, or [(phenyl)-3-(3-phenoxyphenyl)-propyl](dimethyl)-silanes, such as, for example, (4-ethoxyphenyl) [3-(4-fluoro-3-phenoxyphenyl-propyl]dimethyl-silane, sila fluofin Pyrethroids such as allethrin, alphamethrin, bioresmethrin, byfentnnn, cycloprotrin, cyfluthrin, decainethnn, cyhalothrin, cypermene n, deltaiettrin, alpha-yano-3-phenyl-2-methylbenzyl-2,2-dimethyl-3-(2-chloro-2-trifluoro-methylvinyl) cyclopropanecarboxylate, fenpropathrin, fenfluhrin, fenvalerate, flucythrinate, flumethri, fluvalinate, permethrin, resmethrin and tralometirin;

nitroimines and nitromethylenes, such as 1-[(6-chloro-3-pyridinyl)methyl]4,5-dihydro-N-nitro-1H-imidazol-2-amine (imidacloprid), N-[(6-chloro-3-pyridyl)methyl-] $N^2$cyano-$N^1$-methylacetamide (NI-25), abamectin, AC 303, 630, acephate, acrina alanycarb, aldoxycarb, aldrin, ammoniumbifluoride, amitraz, azamethiphos, bacillus thuringiensis, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzron, tefluthrin, temephos, terbufos, tetraclorovinphos, tenhri O-2-tert.-butyl-pyrimidin-5-yl-o-isopropyl-phosphorothiate, thiocyclar, thiofanox, thiometon, tralomedirin, triflumuron, trimethacarb, vamidothion, Verticillium Lacanii, XMC, xylylcarb, benfuracarb, bensultap, bifentrin, bioallethrin, MER-bioallethrin (S)-cyclopentenyl isomer, bromophos, bromophos-ethyl, buprofezin, cadusafos, calcium polysulphide, carbophenothion, cartap, chinomethionate, chlordane, chlorfenvinphos, chlorfluazuron, chlormephos, chloropicrin, chlorpyrifos, cyanophos, beta-cyflutirin, alpha-cypermethrin, cyophenothrin, cyromazine, dazomet, DDT, demeton-S-methylsulphone, diafenthiuron, dialifos, dicrotophos, diflubenzuron, dinoseb, dioxabenzofos, diaxacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramtylnon, hydrogen cyanide, hydroprene, IPSP, isazofos, isofenphos, isoprothiolane, isoxathion, iodfenphos, Kadethrin, lindane, malathion, mecarbam, mephosfolan, mercurous, chloride, metam, Metarthizium, anisopliae, methacrifos, methamidophos, methidathion, methiocarb, methoprene, methoxychlor, methyl isothiocyanate, metholcarb, mevinphos, monocrotophos, naled, Neo-diprion sertifer NPV, nicotine, omethoate, oxydemetonmethyl, pentachlorophenol, petroleum oils, phenothrin, phenthoate, phorate;

Particularly preferred insecticides in this context are:
chlorpyrifos, phoxim, silafluofen, cyfluthrin, cypermethrin, deltamethrin, permethrin, imidacloprid, hexaflumuron, lindane.

The synergistic effect of the mixtres is observed in mixing ratios of from 99:1 to 1:99, preferably from 3:1 to 1:3, and with very particular preference in a ratio of 1:1.

In order to obtain further increased actions against wood-destroying fungi, it is also possible to admix the following fingicides, if desired in addition to those mentioned above.

Triazoles:
amitrole, azocyclotin, BAS 480F, bitertanol, difenoconazole, fenbuconazole, fenchlorazole, fenetanil, fluquinconazole, flusilazole, flutriafol, imibenconazole, isazofos, myclobutanil, Opus, paclobu I,±)-cis-1-(4chlorophenyl)-2-(1H-1,2,4-triazol-1-yl)-cycloheptanol, tetraconazole, triadimefon, triadimenol, triapenthenol, triflumizole, uniconazole;

imidazoles:
imazalil, pefurazoate, prochloraz, triflumizole,2-(1-tert.-butyl)1-(2-chlorophenyl)-3-(1,2,4-triazol-1-yl)-propan-2-ol, triazolcarboxanilides, such as 2',6'-dibromo-2methyl-4-trifluoromethoxy4'-trifluoromethyl-1,3-triazole-5-caboxanilide.

copper salts:
copper sulfate, copper carbonate, copper chloride, copper-ammonia complexes, copperamnine complexes.

zinc salts:
zinc sulfate, zinc carbonate, zinc chloride.

mixed salts:
copper/boron mixtures, copper/chromiumbron mixtures, copper/chromium/arsenic mixtures.

Methyl (E)-2-[2-[6-(2-cyanophenoxy)pyrimidin-4-yloxy] phenyl]3-methoxyacrylate, methyl(E)-2-[2-[6-(2-thioamidophenoxy)pyrimidin-4-yloxy]phenyl]-3-methoxyacrylate, methyl (E)-2-[2-[6(2-fluorophenoxy) pyrimidin-4-yloxy]phenyl]-3-methoxyacrylate, methyl(E)-2-[2-[6(2,6-difluorophenoxy)pymidin-4-yloxy]phenyl]-3-methoxyacrylate, methyl (E)-2-[2-[3-(pyrimidin-2-yloxy] phenoxyl]phenyl]-3-methoxyacrylate, methyl (E)-2-[3-[5-(methylpyhmldin-2-yloxy]phenoxy]phenyl]-3-methoxyacrylate,methyl(E)-2-[2-[3-(phenyl-sulfonyloxy) phenoxy]phenyl]-3-methoxyacrylate, methyl(E)-2-[3-[4-(nitrophenoxy)phenoxy]phenyl]-3-methoxyacrylate, methyl (E)-2-[2-phenoxyphenyl]-3-methoxyacrylate, methyl(E)-2-[2-3,5-dimethylbezyl)pyrrol-1-yl]-3-methoxyacrylate, methyl (E)-2-[2-(3-methoxyphenoxy)phenyl]-3-methoxyacrylate, methyl (E)-2-[2-2-(2-(phenylethen-1-yl) phenyl]-3-methoxyacrylatemethyl (E)-2-[2-3,5-chlorophenoxy)-pyridin-3-yl]3-methoxyacrylate,methyl(E)-2-(2-(3-(1,1,2,2-tetrafluoroethoxy)phenoxy)-phenyl)-3-methoxyacrylate, methyl (E)-2-(2-[3-(alpha-hydroxybenzy) phenoxy)phenyl)-3-methoxyacrylate, methyl (E)-2-(2-(4-phenoxypyridin-2-yloxy)phenyl)-3-methoxyacrylate, methyl (E)-2-[2-3-n-propyloxyphenoxy)phenyl]-3-methoxyacrylate, methyl (E)-2-[2-3-isopropyloxyphenoxy) phenyl]-3-methoxyacrylatemethyl (E)-2-[2-[3-(2-fluorophenoxy)phenoxy]phenyl]-3-methoxyacrylate,methyl (E)-2-[2-(3-ethoxyphenoxy)phenyl]-3-methoxyacrylatemethyl (E)-2-[2-(4-tert.butylpyridin-2-yloxy)phenyl]-3-methoxyacrylate, methyl (E)-2-[2-[3-(3-cyanophenoxy)phenoxy]phenyl]-3-methoxyacrylatemethyl (E)-2-[2-[243-methylpyridin-2-yloxymethyl)phenyl]-3-methoxyacrylate, methyl (E)-2-[2-[6-(2-methylphenoxy) pyrimidin-4-yloxy]phenyl]-3-methoxyacrylate,methyl (E)2-[2-5-bromopyridin-2-yloxymethyl]phenyl]-3-methoxyacrylate, methyl (E)-2-[2-(3-(3-iodopyridin-2-yloxylphenoxy)-phenyl)-3-methoxyacrylate, methyl (E)-2-[2-[6(2-chloropyridin-3-yloxy]pyrimidin-4-yloxy]phenyl]-3-methoxyacrylate, (E),(E)methyl -2-[2-(5, 6dimethylpyrazin-2-ylmethyloximinomethyl)phenyl]-3-methoxyacrylate, (E) methyl-2-{2-[6-[6-methylpyridin-2-yloxy)pyrimidin-4yloxy)phenyl}-3-methoxyacrylate, (E), (E) methyl-2-{2-(3-methoxyphenyl)methyloximinomethyl) phenyl }-3-methoxyacrylate,(E) methyl-2-{2-(6-(2-azidophenoxy)pyrimidin-4-yloxylphenyl}3-methoxyacrylate, (E),(E) methyl-2-{2-[6-phenylpyrimidin4-yl)methyloximino methyl)phenyl}-3-methoxyacrylate, (E),(E) methyl-2-{2-[(4-cglorophenyl) methyloximinomethyl]phenyl}-3-methoxyacrylate, (E) methyl-2-{2-[6-(2-n-propylphenoxy)1,3,5-triazinfyloxy] phenyl}-3-methoxyacrylate, (E),(E)methyl -2-{2-[(3-nitrophenyl)methyloximino methyl)phenyl}-3-methoxyacrylate.

Succinate dehydrogenase inhibitors such as:
fenfurar, flrcarbanil, cyclafluramide, furmecyclox, Seedvax, metsulfovax, pyrocarbolide, oxycarboxin, Shirlan, mebenil (mepronil), benodanil, flutolanil (Moncut)

naphthalene derivatives such as:

terbinafine, naftifine, butenafine, 3-chloro-7-2-aza-2,7,7-trimethyl-oct-3-en-5-ine)

sulfenamides such as dichlorofluanid, tolylfluanid, folpet, fluorfolpet; captan, captofol, benzimidazoles, such as carbendazirn, benomyl, firathiocarb, fuberidazole, thiophonatmethyl, thiabendazole or salts thereof;

thiocyanates such as thiocyanatomethylthiobenzothiazole, methylene bisthiocyanate; quaternary ammonium compounds such as benzyldimethyltetradecylarmmonium chloride, benzyldimethyldodecyclammonium chloride, didecyldimethylammonium chloride, morpholine derivatives such as tridemorph, fenpropimorph, falinorph, dimethomorph, dodemorph; aldimorph, fenpropidin and arylsulfonic salts thereof, for example p-toluenesulfonic acid and p-dodecylphenyl-sulfonic acid, iodine derivatives such as diiodomethyl p-tolyl sulfone, 3-iodo-2-propinyl alcohol, 4 chlorophenyl 3-iodopropargyl fonnal, 3-bromo-2,3-diiodo-2-propenyl ethylcarbate, 2,3,3-triiodallyl alcohol,3-bromo-2,3-diiodo-2-propenyl alcohol, 6iodo-3-oxo-hex-5-inol butylcarbamate, 6iodo-3-oxo-hex-5-in-ol-phenylcarbamate,3-iod-2-propinyl-n-hexylcarbamate, 3-iod-2-propinyl-cyclohexylcarbamate, 3-iodo-2-propinyl phenylcarbamate;

phenol derivatives such as tribromophenol, tetrachlorophenol, 3-methylfhlorophenyl, dichlorophen, o-phenylphenol, m-phenylphenol, p-phenylphenol, 2-benzyl-4-chlorophenol;

glutaraldehyde; bromine derivatives such as 2-bromo-2-nitro-1,3-propanediol;

isothiazolinones, such as N-methylisothiazolin-3-one, 5-chloro-N-methyl-isothiazoline-3-one, 4,5-dichloro-N-octyliso-thiazolin-3-one, Ntyl-isothiazolin-3-one;

benzisothiazolinones, 4,5-trimethylene-isothiazolinones;

pyridines or pyrimidines, such as 1-hydroxy-2-pyridinethione (and their Na, Fe, Mn, Zn salts), tetrachloro-4-methylsulfonylpyridine, pyrimethanil, mepanipyrim, dipyrithion;

metal soaps, such as tin naphthenate, copper naphthenate, zinc naphthenate, tin octoate, copper octoate, zinc octoate, tin 2-eylhexanoate, copper 2-ethylhexanoate, zinc 2-ethylhexanoate, oleate, tin phosphate, copper phosphate, zinc phosphate, tin beneoate, copper benzoate and zinc benzoate;

oxides such as tributyltin oxide, $Cu_2O$, CuO, ZnO;

dialkyldithiocarbamates, such as Na salts and Zn salts of dialkyldithiocarbamates, tetramethylthiuram disulfide;

dithiocarbamates, cuiraneb, ferbam, mancopper, mancozeb, maneb, metam, metirm, thiram zineb, ziram:

nitriles such as 2,4,5,6-tetrachloroisophthalodinitrile, 2,3,5,6-tetrafluoroterephthalodinitrile;

benzthiazoles such as 2-mercaptobenzothiazole; quinolines, such as 8-hydroxyquinoline and Cu salts thereof;

benzamides, such as 2,6dichloro-N(4-trifluoromethylbenzyl)benzamide (XRD-563);

boron compounds, such as boric acid, boric esters, borax;

formaldehyde and formaldehyde-donor compounds, such as benzyl alcohol mono(poly)-hemiformal, oxazolidine, hexa-hydro-S-triazine, N-methylolchloroacetamide, paraformaldehyde, nitropyrin, oxolinic acid, tecloftalam;

tris-N-(cyclohexyldiazeniumdioxy)-aluminium,N-(cyclohexyldiazeniumdioxy)tributyltin and K salts, bis-N-cyclohexyldiazeniumdioxy)-copper.

Furthermore, highly active compounds are also produced with the following active substances:

fungicides acypetacs, 2-aminobutane, ampropylfos, anilazine, benalaxyl, bupirint, chinomethionate, chloroneb, chlozolinate, cymoxanil, dazomet, diclomezine, dichloram, diethofencarb, dimethirimol, dinocab, dithianon, dodine, drazoxolon, edifenphos, ethirimol, etridazole, fenarimol, fenitropan, fentin acetate, fentin hydroxide, ferimzone, fluazinam, fluromide, flusulfamide, flutriafol, fosetyl, fthalide, furalaxyl, guazatine, hymexazol, iprobenfos, iprodione, isoprothiolane, metalaxyl, methasulfocarb, nitrothalisopropyl, nuarimol, oflurace, oxadiyl, perflurazoate, pencycuron, phosdiphen, pimaricin, piperalin, procymidone, propamocarb, propineb, pyrazophos, pyrifenox, pyroquilon, quintozene, tar oils, tecnazene, thicyofen, thiophanate-methyl, tolclofos-methyl, triazoxide, trichlamide, tricyclazole, triforine, vinclozolin.

The weight ratios of the active substances in these active-substance combinations can be varied within relatively large ranges.

The active-substance combinations preferably obtain the insecticidal active substance in a proportion of from 0.1 to 99.9%, in particular from 1 to 75%, particularly preferably from 5 to 50%, the remainder to 100% being made up by one or more of the above-mentioned co-components.

The quantity of the compositions and/or concentrates employed is dependent on the nature and incidence of the insects, microorganisms, on the germ count and on the medium. The optimum quantity for use in the application can be determined in each case by a series of tests. In general, however, it is sufficient to employ from 0.001 to 20% by weight, preferably from 0.05 to 10% by weight, of the active-substance mixture, relative to the material to be protected.

The active-substance mixture can be used as such, in the form of concentrates or generally customary formulations, such as solutions, suspensions, emulsions or pastes.

The formulations mentioned can be prepared in a mnner known per se, for example by mixing the active substances with solvents and/or diluents, emulsifier, dis sant and/or binder or fixative, water repellent, if desired siccatives and UV stabilizers, and, if desired, dyes and pigments, and also firther processing auxiliaries.

The solvent and/or diluent is an organic-chemical solvent or solvent mixtu and/or an oily or oil-like, relatively non-volatile organic-chemical solvent or solvent mixture and/or a polar organic-chemical solvent or solvent mixture and/or water and at least one emulsifier and/or wetting agent or consists thereof As organic-chemical solvents it is preferred to employ oil or oil-like solvents having an evaporation number of more han 35 and a flash point of more than 30° C., preferably more than 45° C. As such relatively non-volatile, water-insoluble, oily and oil-like solvents, use is made of appropriate mineral oils or their aromatic fractions or mineral oil-containing solvent mixtures, preferably white spirit, petroleum and/or alkylbe ee.

Those employed with advantage are mineral oils having a boiling range of from 170 to 220° C., white spirit having a boiling range of from 170 to 220° C., spindle oil having a boiling range of from 250 to 350° C., petroleum or aromatics with a boiling range from 160 to 280° C., turpentine oil and the like.

In a preferred embodiment, use is made of liquid aliphatic hydrocarbons having a boiling range of from 180 to 210° C. or high-boiling mixtures of aromatic and aliphatic hydrocarbons having a boiling range of from 180 to 220° C. and/or spindle oil and/or monochloronaphthalene, preferably α-mmonochloronaphtalene.

The organic, relatively non-volatile oily or oil-like solvents having an evaporation number of more than 35 and a flash point of above 30° C., preferably of above 45° C., can be replaced in part by readily or moderately volatile organic-chemical solvents, with the proviso that the solvent mixture likewise has an evaporation number of more than 35 and a flash point of more than 30° C., preferably more than 45° C., and that the insecticideifungicide mixture is soluble or emulsifiable in this solvent mixture.

In accordance with a preferred embodiment, part of the organic-chemical solvent or solvent mixture is replaced or an aliphatic polar organicchemical solvent or solvent mixture. Preferably, aliphatic organic-chemical solvents containing hydroxyl and/or ester and/or ether groups are used, for example glycol ethers, esters or the like.

As a solvent or diluent, water in particular is also suitable, which may be mixed with one or more of the abovementioned organic-chemical solvents or diluents, emulsifiers and dispersants.

The organic-chemical binders which are used in the context of the present invention are the synthetic resins which are known per se and which are water-ilutable and/or dispersible or emulsifiable or soluble in the organic-chemical solvents employed, and/or binding drying oils, especially binders consisting of or comprising an acrylic resin, a vinyl resin, for example polyvinyl acetate, polyester resin, condensation polymer resin or addition polymer resin, polyurethane resin, alkyd resin or modified alkyd resin, phenolic resin, hydrocarbon resin, such as indene-coumarone resin, silicone resin, drying vegetable and/or drying oils and/or physically drying binders based on a natural and/or synthetic resin.

The synthetic resin used as binder can be employed in the form of emulsion, dispersion or solution. As binders it is also possible to use bitumen or bituminous substances in a proportion of up to 10% by weight. In addition, dyes, pigments, water repellents, odour correctors and inhibitors and/or anticorrosion agents and the like which are known per se can be employed.

According to the invention, it is preferred as organic-chemical binder for at least one alkyd resin or modified alkyd resin and/or a drying vegetable oil to be present in the composition or in the concentrate. It is preferred according to the invention to use alkyd resins having an oil content of more than 45% by weight, preferably from 50 to 68% by weight.

The binder mentioned can be replaced wholly or partially by a fixative (mixture) or a plasticizer (mixture). These additives are intended to prevent volatilization of the active substances and crystallization or precipitation. They preferably replace from 0.01 to 30% of the binder (based on 100% of the binder employed).

The plasticizers derived from the chemical classes of the phthalic esters, such as dibutyl phthalate, dioctyl phthalate or beneyl butyl phthalate, phosphoric esters, such as tributyl phosphate, adipic esters, such as di(2-ylhexyl) adipate, stearates, such as butyl stearate or amyl stearate, oleates, such as butyl oleate, glycerol ethers or relatively high molecular weight glycol ethers, glycerol esters and ptoluenesulfonic esters.

The chemical basis of fixatives, for example, is polyvinyl alkyl ethers, such as polyvinyl methyl ether, or ketones, such as benzophenone and ethylenebenzophenone, or nitrogen compounds such as alklolanines and anmonia.

The wood which can be protected by the active-substance m according to the invention or by compositions containing the latter is to be understood, for example, as: constructional timber, wooden beams, railway sleepers, bridge components, jetties, wooden vehicles, crates, pallets, containers, telephone poles, wooden panelling, wooden windows and doors, plywood, chipboard, joinery work or wooden products which are used quite generally in house building or in joinery.

Particularly effective wood protection is obtained by large-scale industrial impregnation processes, for example vacuurn, double vacuun or pressure processes.

The microbicidal compositions or concentrates used for protecting wood and wooden materials contain the active-substance combination in a concentration of from 0.01 to 95% by weight, in particular from 0.01 to 60% by weight.

Preferred compositions (ready-to-use compositions) preferably contain from 0.2 to 3% by weight, in particular from 0.5 to 2% by weight, of a mixture of Alsystin with fungicides, herbicides and/or algicides and at least one organic-chemical solvent or solvent mixture and/or an oily or oil-like relatively non-volatile organic-chemical solvent or solvent mixture and/or a polar organic-chemical solvent or solvent mixre and/or water and emulsifier and/or wetting agent and, if desired, from 0 to 5% by weight, preferably fiom 0.1 to 3% by weight, of fixative and/or other additional agents as the residual constituent.

Particularly preferred (ready-to-use) compositions contain 2 to 30% by weight, preferably from 5 to 22% by weight, calculated as solids, of a synthetic-resin binder, preferably an alkyd resin and/or a drying vegetable oil, and at least one organic-chemical solvent or solvent mixture and/or an oily or oil-like relatively non-volatile organic-chemical solvent or solvent mixture and/or a polar organic-chemical solvent or solvent mixture and/or water and emulsifier and/or wetting agent and, if desired, siccatives, dyes, colour pigments, anti-settling agents and/or UV stabilizers as the residual constituent.

Concentrates for preserving wood and wooden materials preferably contain from 0.2 to 25% by weight, preferably from 3 to 8% by weight, of a rnixtr of Alsystin with fungicides, herbicides or algicides, from 5 to 40% by weight, preferably from 10 to 30% by weight (calculated as solids), of at least one organic-chemical binder and/or fixative or plasticizer and, in addition, an organic-chemical solvent or solvent mixture and/or an oily or oil-like relatively non-volatile organic-chemical solvent or solvent mixture and/or a polar organic-chemical solvent or solvent mixture and/or a penetration auxiliary and/or water and an emulsifier and/or wetting agent as the residual constituent.

The compositions according to the invention make it possible in an advantageous manner to replace the microbicidal compositions available at present by more effective compositions. They exhibit good stability and, advantageously, have a broad spectrum of action.

EXAMPLE 1

Instead of the direct testing of balanides, Arternia salina was used in searching for substances having a development-inhibiting effect on Crustaceae.

This saltwater crustacean is highly suitable because of its many larval stages and the established test systems, which are recognized internationally. Because of the different sensitivities of the nauplius stages, synchronized populations were used for testing (R. B. Sleet and K. Brendel: Homogeneous populations of Artemia nauplii and their potential etc for in vitro testing in developmental toxicology, Teratogenesis, Carcinogenesis and Mtagenesis 5; 41–54 (1985)). The tests were carried out in accordance with the procedure published by Sorgeloos and co-workers (P. Sorgeloos, C. R van der Wielen and G. Persoone: The use of Artemia nauplii for toxicity tests—a critical analysis, Ecotoxicology and Environmental Sefety 2, 249-255 (1978)).

Rating: 3=100% mortality
2=50%, <100% mortality
1=20–50% mortality
0=no action

TABLE 1

Result for some compounds according to the invention

| Active substance | µg of active substance per ml of incubation medium | Rating |
| --- | --- | --- |
| Alsystin | 10 | 3 |
| Chlorofluazuron | 10 | 3 |
| Methoprene | 100 | 3 |
|  | 10 | 1–2 |
| Hydroprene | 100 | 3 |
| Pyriproxylen | 100 | 3 |
|  | 10 | 3 |

We claim:

1. An anti-fouling composition comprising:
  a) an anti-fouling effective amount of at least one insecticide selected from the group consisting of;
   i) triflumuron;
   ii) chlorfluazuron;
   iii) diflubenzuron;
   iv) flufenoxuron;
   v) flucycloxuron;
   vi) hexaflumuron;
   vii) penfluron;
   viii) teflubenzuron;
   ix) 1-[(6-chloro-3-pyridinyl)-methyl]-4,5-di hydro-N-nitro-1H-imdazol-2-amine (imidacloprid);
   x) N-[(6chloro-3-pyridinyl)-methyl]-$N^2$-cyano-$N^1$-methylacetarnide (NI-25);
   xi) 1-[4-(4chlorophenoxy),3,5-dichlorophenyl]-3-(2,6-difluorobenzoyl)-urea; and
   xii) N-[[[2,5dichloro-4-(1,1,2,3,3,3-hexafluoropropoxy)phenyl]-amino]-carbonyl]-2,6-difluorobenzamide;
  b) a carrier; and
  c) a binder selected from the group consisting of
   i) solvent systems comprising polyvinyl chloride;
   ii) solvent systems comprising chlorinated rubber;
   iii) aqueous dispersions comprising vinyl chloride/vinyl acetate copolymers;
   iv) organic solvent systems comprising vinyl chloride/vinyl acetate copolymers;
   v) butadiene/styrene rubbers;
   vi) butadiene/acrylonitrile rubbers;
   vii) butadiene/styrene/acrylonitrile rubbers;
   viii) drying oils;
   ix) asphalt;
   x) epoxy compounds;
   xi) resin esters or modified hard resins in combination with tar or bitumen;
   xii) chlorinated rubber;
   xiii) chlorinated polypropylene; and
   xiv) vinyl resins.

2. An anti-fouling composition according to claim 1, additionally comprising at least one algicide, herbicide, fungicide, molluscicide or other compound exhibiting anti-fouling activity.

3. An anti-fouling composition according to claim 1, wherein the insecticide is selected from the group consisting of triflumuron and chlorfluazuron, and the anti-fouling composition further comprises at least one algicide, herbicide, fungicide, molluscicide or other compound exhibiting anti-fouling activity.

4. A method of protecting articles which come into contact with seawater and brackish water, said method comprising applying to such articles an anti-fouling effective amount of an anti-fouling composition comprising:
  a) an anti-fouling effective amount of at least one insecticide selected from the group consisting of:
   i) triflumuron;
   ii) chlorfluazuron;
   iii) diflubenzuron;
   iv) flufenoxuron;
   v) flucycloxuron;
   vi) hexaflumuron;
   vii) penfluron;
   viii) teflubenzuron;
   ix) 1-[(6-chloro-3-pyridinyl)-methyl]4,5-dihydro-N-nitro-1H-imidazol-2-amine (imidacloprid);
   x) N-[(6-chloro-3-pyridinyl)-methyl]-$N^2$-cyano-$N^1$-methylacetamide (NI-25);
   xi) 1-[4-(4-chlorophenoxy)-3,5-dichlorophenyl]-3-(2,6-difluorobenzoyl)-urea; and
   xii) N-[[[2,5-dichloro-4-(1,1,2,3,3,3-hexafluoropropoxy)-phenyl]-amino]-carbonyl]-2,6-difluorobenzamide;
  b) a carrier; and
  c) a binder.

5. The method according to claim 4, wherein a surface of the article to be protected comprises wood.

6. The method according to claim 4, wherein said anti-fouling composition further comprises at least one algicide, herbicide, fungicide, molluscicide or other compound exhibiting anti-fouling activity.

7. The method according to claim 4, wherein the insecticide is selected from the group consisting of triflumuron and chlorofluazuron, and the anti-fouling composition further comprises at least one algicide, herbicide, fungicide, molluscicide or other compound exhibiting anti-fouling activity.

* * * * *